United States Patent [19]
Doerge

[11] Patent Number: 5,371,102
[45] Date of Patent: Dec. 6, 1994

[54] COMPOSITIONS AND METHODS OF INHIBITING THYROID ACTIVITY

[75] Inventor: Daniel Doerge, Little Rock, Ark.

[73] Assignee: University of Hawaii, Honolulu, Hi.

[21] Appl. No.: 103,813

[22] Filed: Aug. 6, 1993

Related U.S. Application Data

[63] Continuation of Ser. No. 849,669, Mar. 11, 1992, abandoned.

[51] Int. Cl.$^5$ ............... A61K 31/505; A61K 31/415; A61K 31/17
[52] U.S. Cl. .................... 514/387; 514/274; 514/392; 514/580; 514/584
[58] Field of Search ............... 514/274, 387, 392, 580, 514/584

[56] References Cited

U.S. PATENT DOCUMENTS

| | | | |
|---|---|---|---|
| 3,499,085 | 3/1970 | Sasse et al. | 424/273 |
| 3,704,239 | 11/1972 | Wei et al. | 260/306.7 |
| 4,205,077 | 5/1980 | Aufderhaar et al. | 424/273 B |
| 4,215,134 | 7/1980 | Ross et al. | 424/273 B |
| 4,814,329 | 3/1989 | Harányi et al. | 514/211 |
| 4,873,346 | 10/1989 | Anderson | 548/157 |
| 4,925,854 | 5/1990 | Schöllkopf et al. | 514/338 |
| 4,948,792 | 8/1990 | Kappas et al. | 514/185 |

OTHER PUBLICATIONS

CA 95(21): 181433y, Redmond et al., 1981.
Duffin et al., "Anhydro-compounds from Nitrogen-containing Derivatives of Thioglycollic Acid. Part II. Glyoxaline and Benziminazole Compounds", J. Chem. Soc., pp. 361–364 (1956).
Raby, et al., "The Mechanism of Action of Synthetic Antithyroid Drugs: Iodine Complexation During Oxidation of Iodide", Endocrinology, vol. 126, No. 3, pp. 1683–1691 (1990).
De Groot et al., "Iodide Transport in Other Organs", Hormone Synthesis, Secretion, and Action, pp. 42–56 (1960).
Engler, et al., "Mechanism of Inactivation of Thyroid Peroxidase by Thioureylene Drugs", Biochemical Pharmacology, vol. 31, No. 23, pp. 3801–3806 (1982).
Doerge, D. R., "Mechanism-Based Inhibition of Lactoperoxidase by Thiocarbamide Goitrogens", Biochemistry, vol. 25, pp. 4724–4728 (1986).
Doerge, D. R., "Mechanism-Based Inhibition of Lactoperoxidase by Thiocarbamide Goitrogens. Identification of Turnover and Inactivation Pathways", Biochemistry, vol. 27, pp. 3697–3700 (1988).
Cooper, D. S., "Antithyroid Drugs", The New England Journal of Medicine, vol. 311, No. 21, pp. 1353–1362 (Nov. 22, 1984).
Doerge, et al., "Organosulfur Oxygenation and Suicide Inactivation of Lactoperoxidase", Biochemical Pharmacology, vol. 36, No. 6, pp. 972–974 (1987).
Wagner, et al., "Benzimidazole", pp. 65–66 (1941).
Kikugawa, Y., "A Facile N-Alkylation of Imidazoles and Benzimidazoles", pp. 124–125, (1981).
Karkhanis et al., "Thiono Compounds. 5. Preparation and Oxidation of Some Thiono Derivatives of Imidazoles", Phosphorus and Sulfur, vol. 22, pp. 49–57, (1985).
Doerge, D. R., "Synthesis of $^{14}$C- and 5S-Labelled 2-Mercaptobenzimidazoles", Journal of Labelled Compounds and Radiopharmaceuticals, vol. XXV, No. 9, pp. 985–990 (1988).

(List continued on next page.)

Primary Examiner—Marianne M. Cintins
Assistant Examiner—Kimberly R. Jordan
Attorney, Agent, or Firm—Limbach & Limbach

[57] ABSTRACT

Methods of using N,N'-disubstituted thiocarbamide compounds for reversibly inhibiting hyperthyroidism are provided. Active compounds reversibly inhibit catalytic iodination without producing sulfenic acid intermediates which can permanently inactivate thyroid peroxidase. By preventing sulfenic acid formation, side effects due to toxicity in liver and bone marrow can be reduced compared to currently used drugs. The compounds can be formulated for administration to a hyperthyroid patient until remission occurs with less risk of possible everdosing.

17 Claims, 12 Drawing Sheets

OTHER PUBLICATIONS

Weller, et al., "Enzymatic Reduction of 5–-Phenyl-4-pentenyl-hydroperoxide: Dectection of Peroxidases and Identification of Peroxidase Reducing Substrates", Archives of Biochemistry and Biophysics, vol. 243, No. 2, pp. 633-643 (Dec. 1985).

Drabowicz, et al., "A Facile and Selective Oxidation of Organic Sulphides to Sulphoxides with Hydrogen Peroxide/Selenium Dioxide System", pp. 758-759 (1978).

Rahemtulla et al., "Purification and Characterization of Human Salivary Peroxidase", Biochemistry, vol. 27, pp. 233-239 (1988).

Doerge, et al., "Mechanism of Thyroid Peroxidase Inhibition by Ethylenethiourea", Chemical Research in Toxicology, vol. 3, No. 2, pp. 98-101 (1990).

Davis, et al., "Chemistry of Sulfenic Acids. 7. Reason for the High Reactivity of Acids. Stabilization by Intramolecular Hydrogen Bonding and Electronegativity Effects", J. Org. Chem., vol. 51, No. 7, pp. 1033-1040 (186).

Kice, J. L., "Mechanisms and Reactivity in Reactions of Organic Oxyacids of Sulfur and their Anhydrides", pp. 65-181 (1980).

Shindler, et al., "Peroxidase from Human Cervical Mucus", Eur. J. Biochem., vol. 25, pp. 325-331 (1976).

Nakamura, et al., "Thyroid Peroxidase Selects the Mechanism of Either 1- or 2-Electron Oxidation of Phenols, Depending on Their Substituents", The Journal of Biological Chemistry, vol. 260, No. 25, pp. 13546-13552 (Nov. 5, 1985).

Engler, et al., "Reversible and Irreversible Inhibition of Thyroid Peroxidase-Catalyzed Iodination by Thioureylene Drugs", Endocrinology, vol. 112, No. 1, pp. 86-95 (1983).

Magnusson et al., "Mechanisms of Thyroid Peroxidase and Lactoperoxidase-catalyzed Reactions Involving Iodide", The Journal of Biological Chemistry, vol. 259, No. 22, pp. 13783-13790 (Nov. 25, 1984).

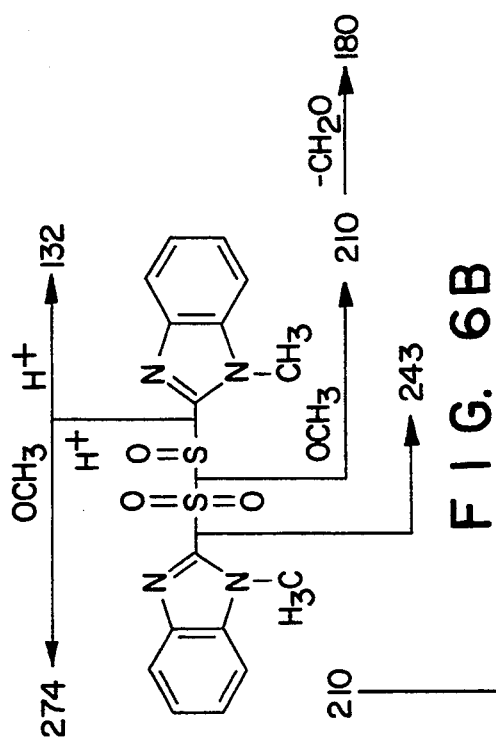
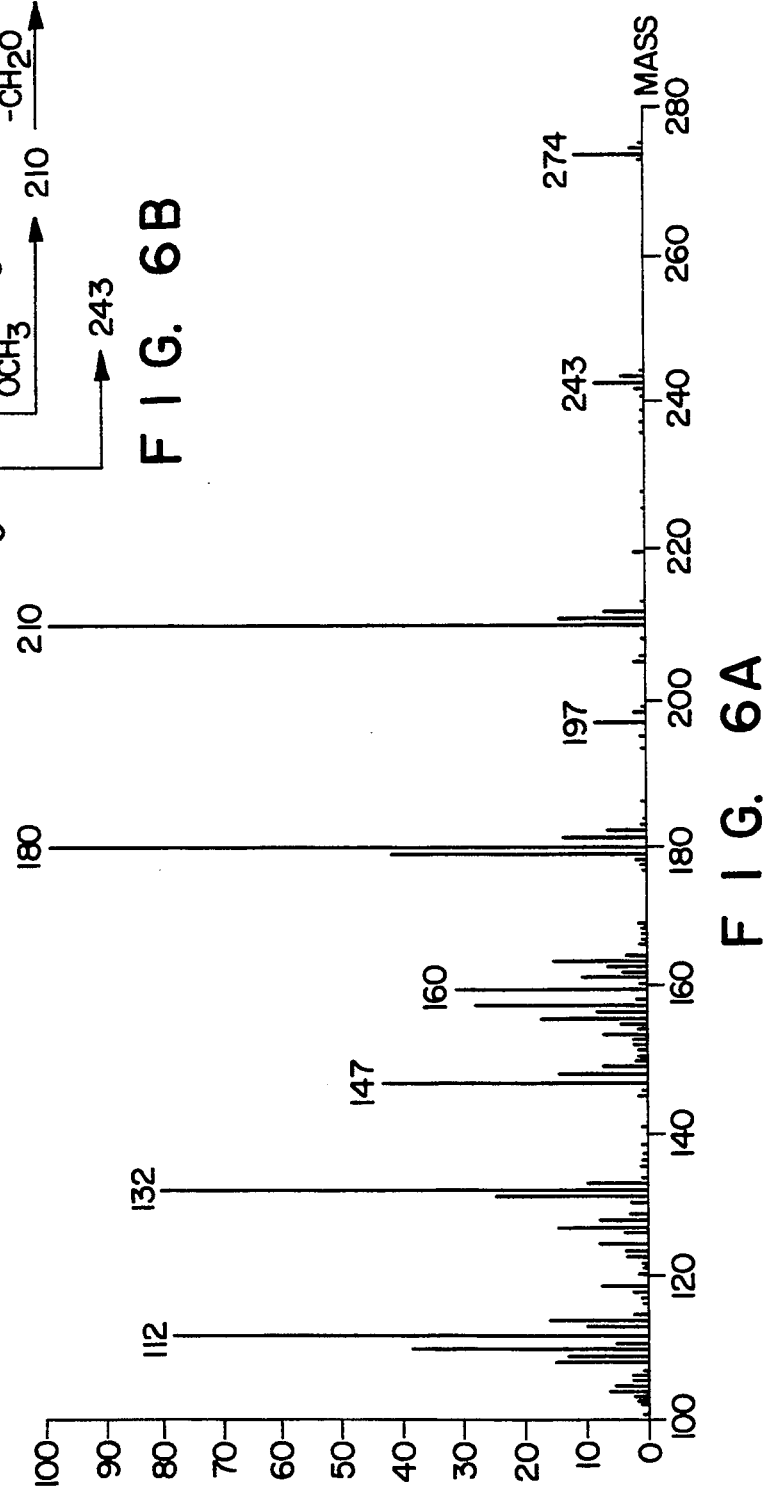
FIG. 6B
FIG. 6A

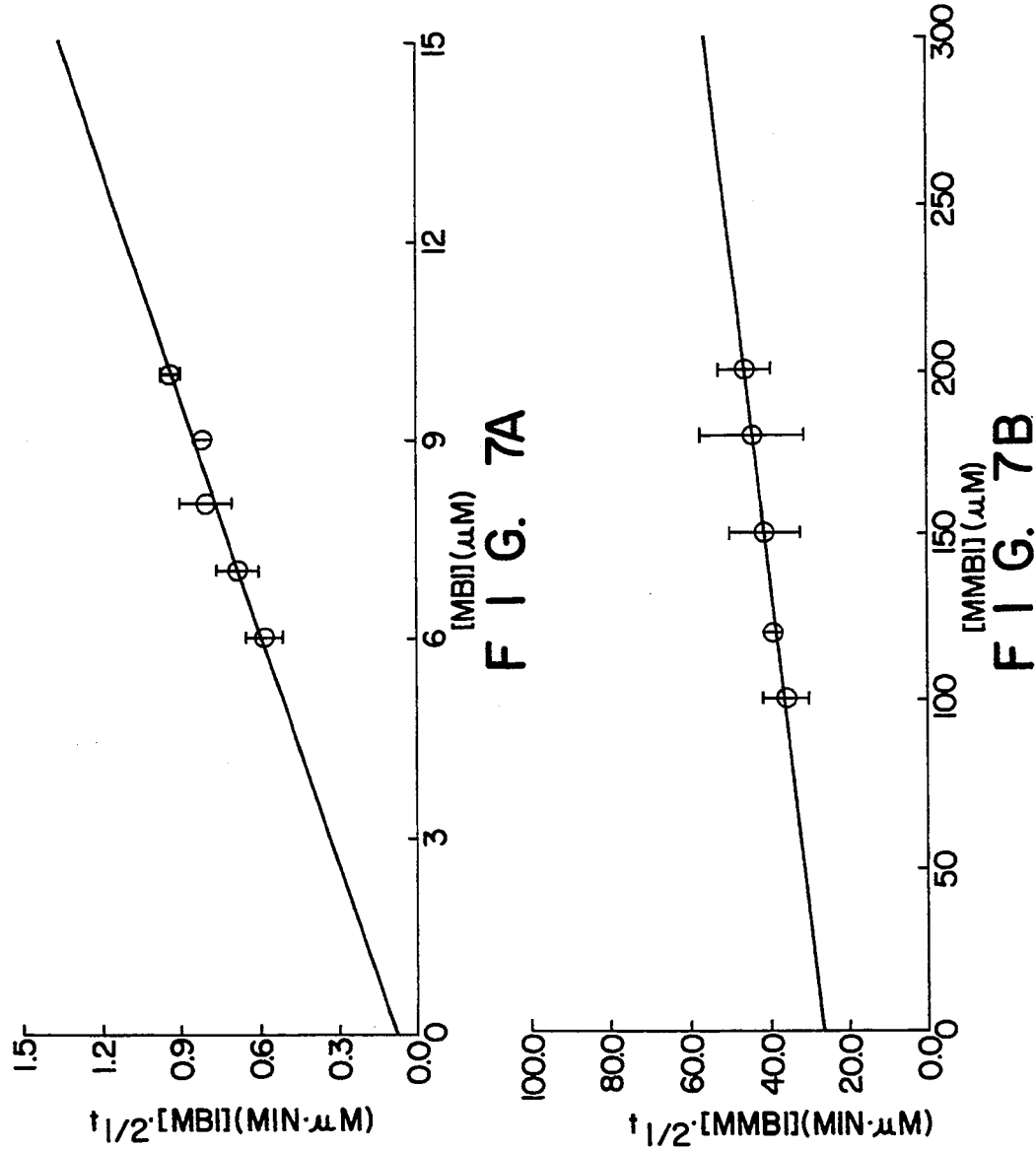

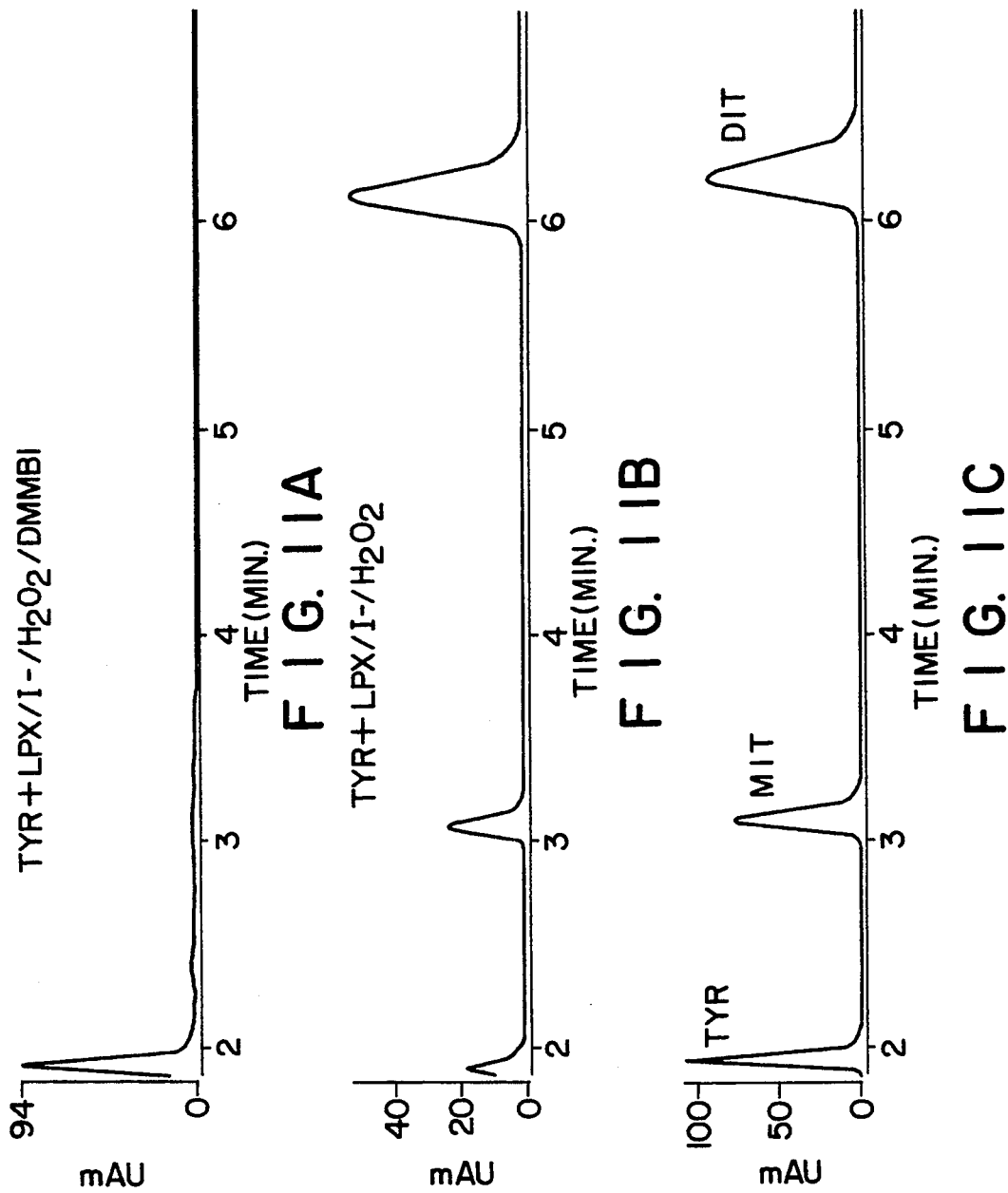

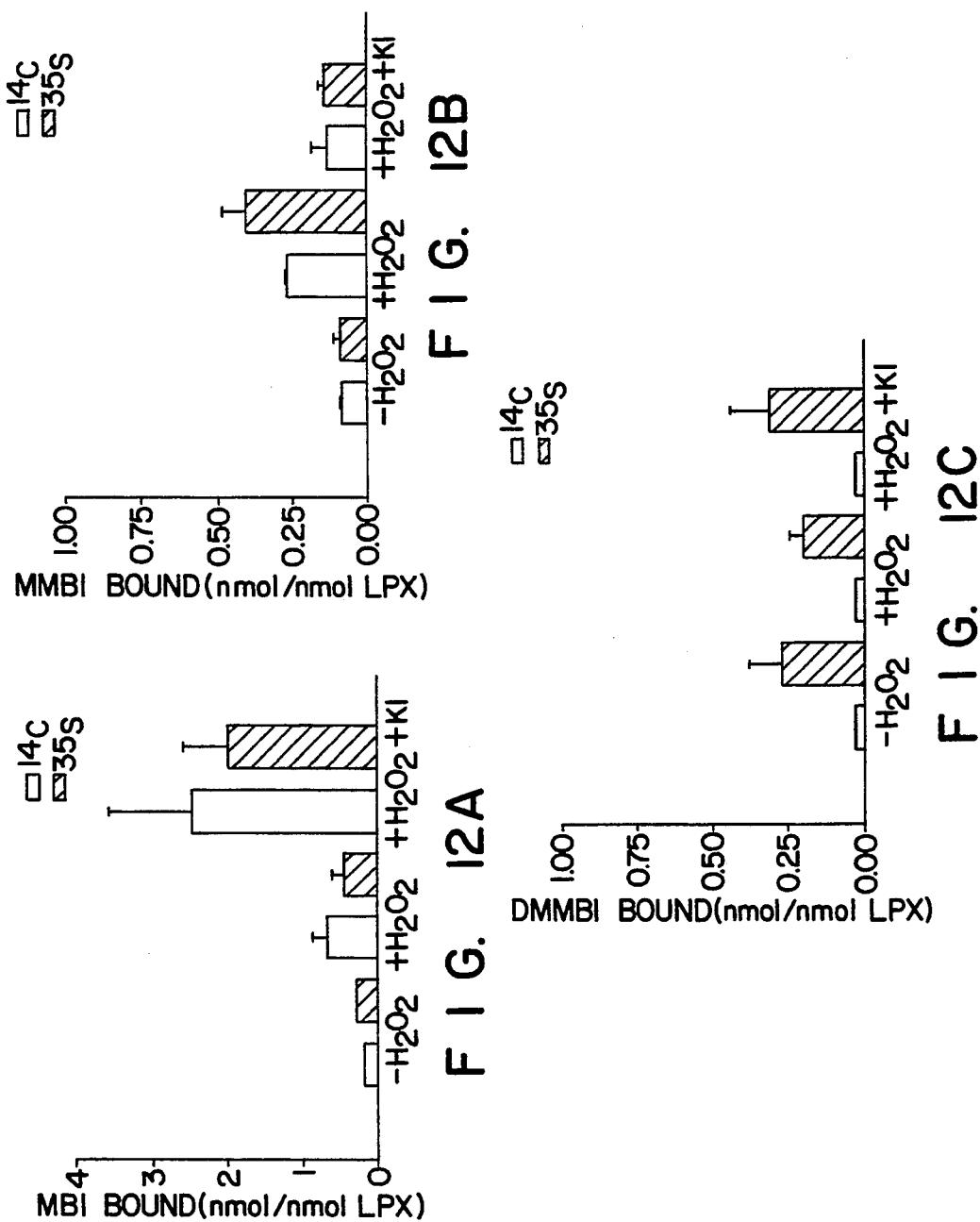

COMPOSITIONS AND METHODS OF INHIBITING THYROID ACTIVITY

This is a continuation of co-pending application Ser. No. 07/849,669 filed on Mar. 11, 1992, now abandoned.

FIELD OF THE INVENTION

The invention relates to anti-hyperthyroid therapy. In particular, the invention involves methods for reversibly inhibiting thyroid activity with N,N'-disubstituted thiocarbamide compounds.

BACKGROUND OF THE INVENTION

The thyroid gland, located in front of the windpipe, secretes the hormone thyroxine into the blood to regulate heart rate, body temperature and calorie consumption. When excess thyroid hormone is produced, a condition known as hyperthyroidism results.

Hyperthyroidism is usually caused by Graves' disease, a condition in which the body overproduces antibodies that specifically stimulate the thyroid gland. The majority of hyperthyroid patients are women. The typical patient becomes nervous, irritable, warm and has difficulty sleeping. The patient's skin is soft and velvety. Although appetite may increase, the patient still loses weight. Other symptoms include tremors, heavier periods and increased frequency of miscarriage. Fluid accumulation behind the eyeballs may move them forward, creating a wide-eyed appearance. Hyperthyroidism is lift-threatening if not treated.

There are presently three primary options for treating hyperthyroidism: 1) drug therapy to block production of thyroid hormones; 2) surgical removal of the thyroid gland; and 3) radioiodide treatment to permanently destroy thyroid gland function. A principal problem with either surgery or radioiodide treatment is that these procedures often cause irreversible hypothyroidism. Hypothyroidism, also known as myxedema, is a life-threatening disease state if untreated. Myxedema affects most major organ systems, for example, cardiovascular, renal, thermoregulation, digestion and respiratory. Since thyroid hormones play a vital role in normal cellular metabolism, treatment of hypothyroidism requires daily dosing of such patients with a pharmaceutical thyroid hormone preparation. Therefore, the more drastic and permanent therapies for hyperthyroidism are usually used only after drug therapy has been unsuccessfully tried or otherwise ruled out.

Drugs which inhibit the formation of thyroid hormones are usually administered orally. After taking the medicine for a few months to several years, about half the patients will exhibit remission of hyperthyroidism, 70 to 80% permanently. Wartofsky, L., McCall's, Nov. 1989, p.106. The primary advantage of anti-hyperthyroid drugs is that they do not cause permanent hypothyrodism and can be discontinued when remission of hyperthyroidism occurs. However, the anti-hypothyroid drugs typically cause permanent enzyme inactivation which can result in periods of hyperthyroidism after termination of drug therapy. The drugs which are most often used to treat hyperthyroidism are the thiourea derivatives propylthiouracil (PTU) and methimazole (MMI), both of which are available from Eli Lilly & Co.

There are two primary problems with anti-hyperthyroid drugs which are currently used today. The first problem is that PTU and MMI are "suicide" inhibitors of thyroid peroxidase (TPX) and the closely related model enzyme, lactoperoxidase (LPX). In this context, "suicide" means that once an enzyme molecule is inhibited by one of these drugs it is permanently inactivated. Thus, after three to four weeks of therapy, the doses of these anti-hyperthyroid drugs often require downward adjustment to prevent hypothyrodism.

A second problem with currently used anti-hyperthyroid drugs is their adverse side effects. Examples of side effects which are known to be caused by these drugs are skin rash, fever, arthralgias and life-threatening agranulocytosis. Cooper, D.S., Antithyroid drugs, The England Journal of Medicine, Vol.311, No. 21, Nov. 22, 1984 p. 1358.

SUMMARY OF THE INVENTION

In view of the problem mentioned above associated with current anti-hypothyroid therapies, an object of the present invention is to provide therapeutic compositions and methods for treatment of hyperthyroidism by reversibly inhibiting thyroid enzyme activity. Anther object of the present invention is to provide therapies for hyperthyroidism which may be effectively administered to humans without causing the number or degree of adverse side effects which are known to be caused by administering prior anti-hyperthyroid drugs.

The objectives stated above are accomplished by first providing an active compound in accordance with the following chemical formula:

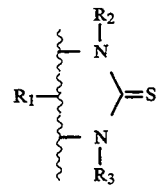

wherein $R_1$ is selected from the group consisting of:

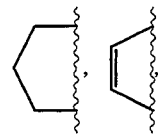

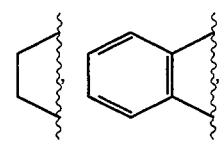

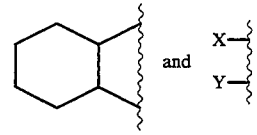

wherein $R_2$, $R_3$, X and Y are independently selected from the group consisting of $C_1$–$C_6$ alkyl and acyl moieties.

A therapeutic dose of the compound is preferably formulated with a suitable carrier, and administered to a patient who is experiencing hyperthyroidism until remission occurs.

Unlike prior anti-hyperthyroid drugs, the compounds employed in the present invention inhibit thyroid activity without permanently inactivating thyroid enzymes. Administration of these compounds, therefore, allows greater therapeutic flexibility because thyroid enzyme inhibition in patients which experience hyperthyroid remission can be reversed.

Experimental studies indicate that appropriate N,N'-disubstituted thiocarbamide compounds cannot form the sulfenic acid intermediates which irreversibly bind to the active site in TPX and LPX enzymes. Thus, $R_2$ and $R_3$ may be varied so long as the compound does not form sulfenic acid intermediates when oxidized by TPX. According to the present invention, methods are described for experimentally determining whether a given thiocarbamide compound derivative tends to form sulfenic acid intermediates and whether it irreversibly inactivates TPX.

BRIEF DESCRIPTION OF THE FIGURES

FIGS. 6A and 6B are graphic plots showing fast atom bombardment mass spectral analysis of the product of MMBI oxidation.

FIG. 7A is a graphic plot of $t_{\frac{1}{2}}$ vs. MBI concentration, showing LPX inactivation by MBI.

FIG. 7B is a graphic plot of $t_{\frac{1}{2}}$ vs. MMBI concentration, showing LPX inactivation by MMBI.

FIGS. 11A, 11B and 11C are chromatographic plots showing that DMMBI inhibits tyrosine iodination.

FIGS. 12A, 12B and 12C show graphic plots comparing covalent binding of labelled substrates, MBI, MMBI, and DMMBI to LPX under metabolic conditions.

DETAILED DESCRIPTION OF THE INVENTION

Figure 1:
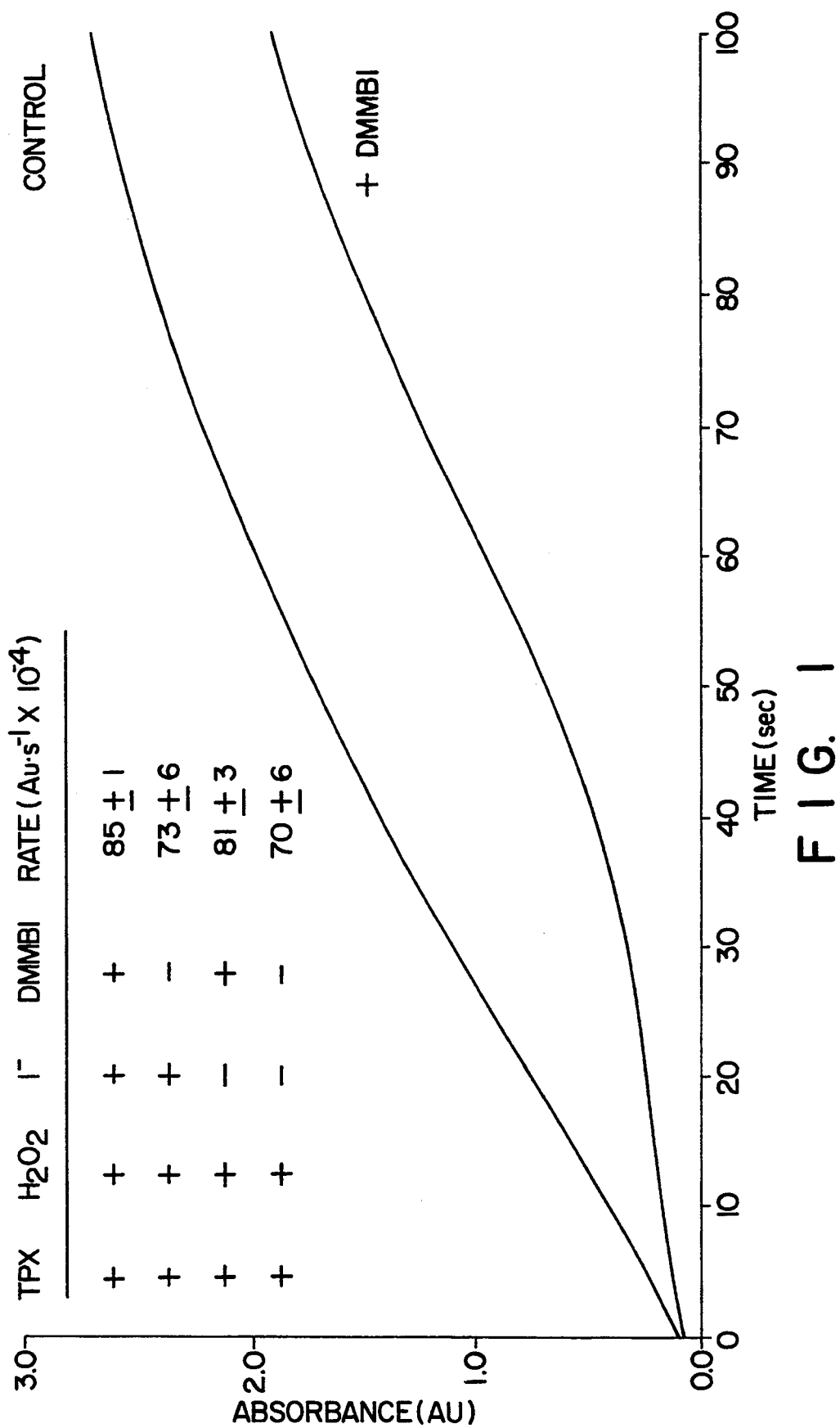
FIG. 1 is a graphic plot of spectrophotometric absorbance vs. time, showing the effect of DMMBI on enzymatic iodination. The inset chart shows the effect of DMMBI on the rate of TPX activity.

The present invention involves new therapeutic methods for treating hyperthyroidism. Previous anti-hyperthyroid drugs such as methimazole and propylthiouracil are "suicide inhibitors" of thyroid peroxidase (TPX) and lactoperoxidase (LPX). In contrast, the compounds employed in the present invention are advantageous in that they inhibit iodination, i.e. production of thyroid hormones, without permanently inhibiting TPX.

The compounds employed in the present invention were discovered as a result of experiments with currently used hyperthyroid drugs to determine the mechanism for suicide inhibition of peroxidases. It has been discovered that permanent inactivation of TPX and LPX results from intermediate oxidation products which covalently bind to the peroxidase heme. By identifying and characterizing the intermediate which is believed to be responsible for peroxidase inactivation, it was possible to conceive and produce compounds which inhibit iodination by a reversible mechanism.

Thus, oxidation of a series of N-substituted benzimidazone-2-thiones by chemical and enzymatic reagents have been investigated. From the qualitative and quantitative differences observed, a pattern linking mechanisms of chemical and enzymatic oxidation are now understood, allowing identification of new advantageous compounds for treating hyperthyroidism in accordance with the present invention.

The present invention involves administering a therapeutically effective dose of a compound in accordance with the following formula:

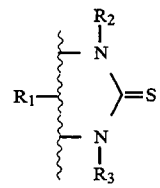

wherein $R_1$ is selected from the group consisting of:

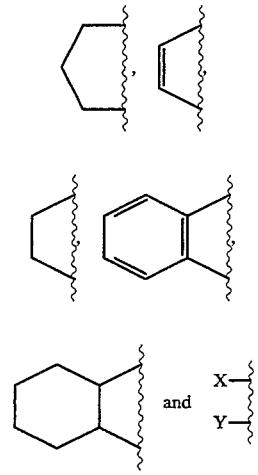

wherein $R_2$ and $R_3$ are independently selected from the group consisting of $C_1$-$C_6$ alkyl moieties and X and Y are independently selected from the group consisting of $C_1$-$C_6$ alkyl and acyl moieties.

The group of compounds which are employed in the present invention were discovered by first studying the mechanism by which currently used drugs such as MMI, permanently inhibit peroxidase enzymes. Similar oxidation products have been observed to be produced by the compounds, methimazole (MMI), benzimidazole-2-thione (MBI), and 1-methylbenzimidazole-2-thione (MMBI). Therefore, MMBI was selected as the model compound representative of imidazoline-2-thione suicide inhibitors, to be used in studies to elucidate their inhibitory mechanism. MMI, MBI, MMBI and DMMBI have the following chemical structures:

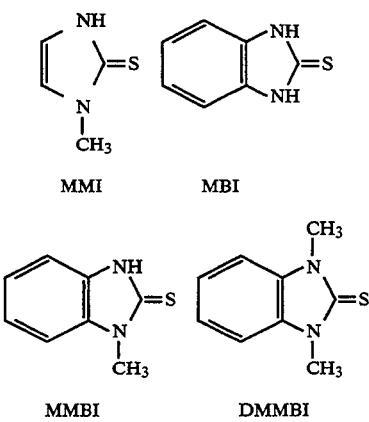

MBI and MMBI are suicide inhibitors of LPX and TPX although the potency diminishes markedly upon N-substitution of MBI. The suicide inhibitors are completely oxidized by 2 equivalents of peroxidative chemical reagents.

The reaction of MMBI with hydroperoxides is believed to proceed first to the benzimidazole-2-sulfenic acid as shown below:

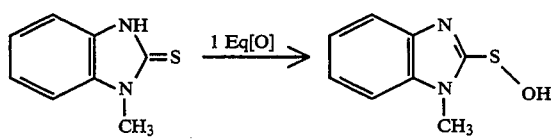

The sulfenic acid intermediate is highly reactive and easily reacts to form the thiosulfinate dimer. The thiosulfonate dimer is believed to have the following structure:

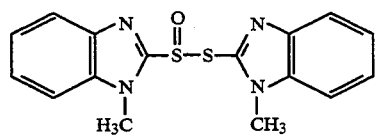

Subsequent oxidation of the dimer by excess hydroperoxide forms the sulfinylsulfone as the terminal product. The sulfinylsulfone is believed to have the following structure:

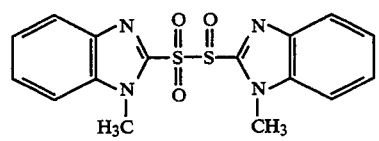

Chemical oxidation of MMBI by hydroperoxides consumes 2 equivalents of oxidant per mole of thione, forms a single product that is stable in the presence of excess oxidant and produces no intermediates under conditions of incomplete oxidation. Chromatographic analysis of the product [gas chromatography (GC), liquid chromatography/thermospray mass spectometry (LC/TSP MS), thin layer chromatography (TLC)] causes the decomposition to MeBI, the sulfinic acid methyl ester and bisulfite ion. These products are consistent with a solvolysis mechanism for the sulfinylsulfone in aqueous methanol as follows:

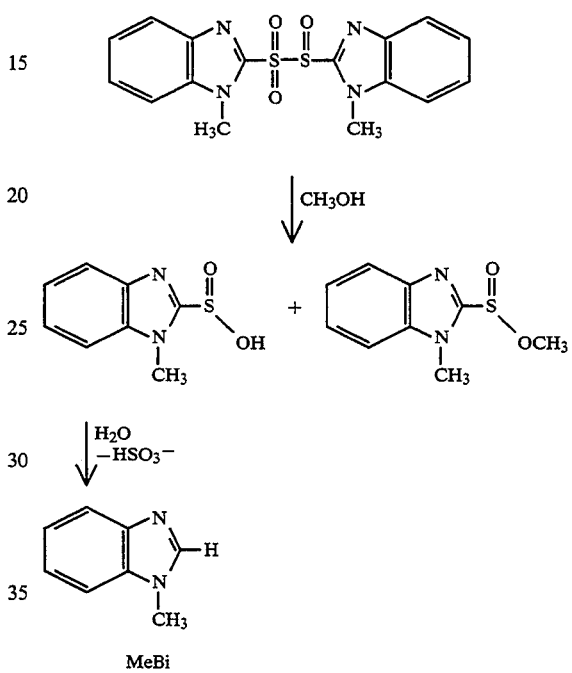

Nucleophilic attack of methanol or water at the sulfinyl sulfur forms one mole each of the methyl ester and the acid or two moles of the acid, respectively. Treatment of reaction mixtures with methylating reagents (e.g. $CH_2N_2$) does not produce detectable sulfinic acid methyl ester. Since no evidence for the existence of the acid has been found, it appears that loss of $SO_2$ is a facile reaction that produces MeBI and bisulfite ion. Since the initial oxidation product is stable in aqueous methanol, it is likely that surface interactions during TLC, LC and GC catalyze the decomposition, especially at elevated temperatures.

The primary MMBI oxidation product has been analyzed by direct insertion probe mass spectrometry. While limited direct evidence for the sulfinylsulfone structure has been seen, the results taken together provide strong support for the proposed structure. Fast atom bombardment mass spectrometry data, discussed in the examples below, is evidence of sulfinylsulfone formation which supports the theory that MMBI oxidation yields 1-methyl-benzimidazoline-2-sulfenic acid as a reactive intermediate.

1-Methyl-benzimidazoline-2-sulfenic acid is the type of reactive intermediate which is believed to be responsible for covalent binding to the prosthetic heme of LPX and TPX during suicide inactivation by imidazoline-2-thiones. The proposed mechanism is consistent with the observed products which form concomitant to MMBI inactivation of LPX. Formation of a thiolsulfinate in an aqueous environment would be followed by hydrolysis to yield MeBI and bisulfite ion from decomposition of the sulfinic acid. These are the only products observed. Doerge, D.R., Biochemistry, Vol. 27, pp.3697-3700 (1988). Alternatively, the sulfenic acid could undergo a second oxidation by LPX compound I to directly form the sulfinic acid which could also bind to the prosthetic heme or form the observed products.

In contrast, oxidation of DMMBI, an N,N'-disubstituted thiocarbamide compound of the present invention, in aqueous methanol requires 3 equivalents of hydroperoxide and the sole products are DMeBI+ and sulfate ions as shown below:

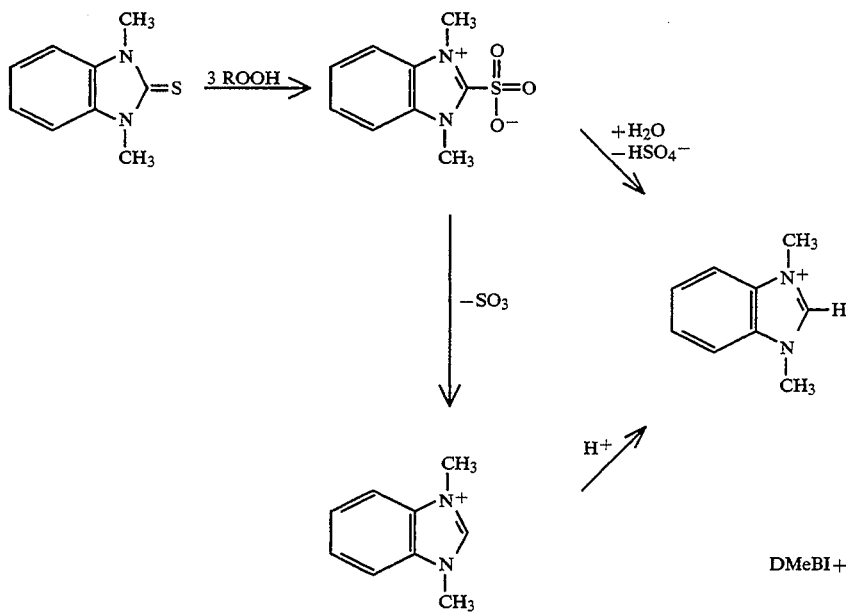

Oxidation of N,N'-dimethylimidazole-2-thione by hydrogen peroxide in aqueous methanol produces the analogous imidazolium and sulfate ions. Karkhanis, et al., Phosphorus and Sulfur, Vol. 22, pp. 49-57 (1985). Because DMMBI is N,N'-disubstituted, no tautomeric proton is present and therefore sulfenic acid formation cannot occur as it can with protonated derivatives like MBI and MMBI.

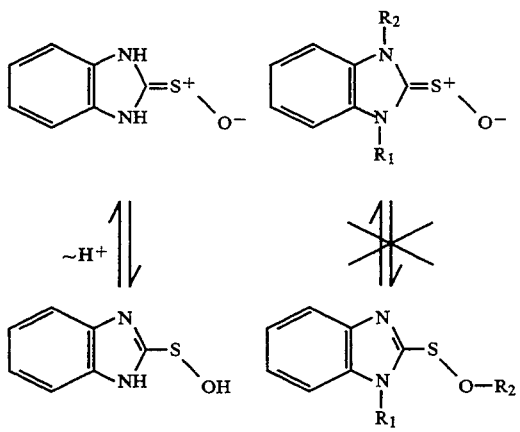

It is believed that, because of this structural limitation, oxidation proceeds to the sulfonyl state only for disubstituted derivatives like DMMBI. The sulfonyl ylide formed protonates to yield DMeBI+ and sulfate ions; in aqueous media.

The differences between DMMBI and MBI/MMBI are equally apparent when the effects on LPX-catalyzed reactions are considered. In the presence of LPX or TPX and hydrogen peroxide, MBI and MMBI cause rapid, irreversible enzyme inactivation and small amounts of turnover products are observed. Surprisingly, DMMBI does not inactivate LPX or TPX or become oxidized under analogous conditions. Unlike the suicide inhibitors, DMMBI does not affect LPX or TPX/hydrogen peroxide-catalyzed oxidation of the substrates ABTS and guaiacol. These substrates are oxidized by the Compound I and II forms, respectively, of peroxidases. DMMBI inhibits only iodide ion oxidation catalyzed by LPX or TPX/hydrogen peroxide. The physiological acceptors for TPX-catalyzed iodination are tyrosine and monoiodo tyrosine residues of thyroglobulin. This mechanism is similar to the alternate substrate mechanism by which imidazolidine-2-thione (ETU) inhibits TPX- and LPX-catalyzed iodination reactions. Doerge et al., Chem. Res. Toxicol., Vol.3, pp.98-101 (1990).

The mechanism of DMMBI inhibition is similar to that described for carbimazole (1-carboxyethyl-3-methylimidazole-2-thione), another "reversible inhibitor" of TPX. However, the carbamoyl ester linkage in carbimazole is labile in vivo and is rapidly converted to methimazole, a suicide inhibitor. As previously proposed for ETU, DMMBI does not react with LPX Compounds I or II but instead, the enzymatic iodinating intermediate.

Reaction of DMMBI with LPX in the presence of 3 equivalents of hydrogen peroxide and iodide ion results in the quantitative conversion of DMMBI to DMeBI+ and sulfate ions. The 3:1 stoichiometry of hydrogen peroxide to reaction products is identical to what was observed in the chemical oxidation studies. The oxidation of DMMBI does not induce LPX inactivation under conditions where >300 turnover events take place. However, these data are consistent with a mechanism involving DMMBI oxidation by LPX-generated oxidized iodine species (e.g., $I_2$, $I^+$, HOI, $I_3^-$) since the same products and stoichiometry are seen from oxidation of DMMBI by chemically formed triiodide ion.

The experimental examples discussed below provide support for the importance of imidazole-2-sulfenic acids, produced from currently used anti-hyperthyroid drugs, as reactive intermediates which cause suicide inactivation of LPX and TPX. The proposed mechanism for enzyme inactivation requires thione oxidation to the sulfenic acid by peroxidase Compound I with subsequent covalent binding to the prosthetic heme. Thus, compounds like MBI, MMBI, and MMI which are capable of forming sulfenic acids are suicide inhibitors.

In contrast, N,N'-disubstituted thiocarbamide compounds which are incapable of forming sulfenic acid are not suicide inhibitors. The following compounds are exemplary chemical structures of the present invention.

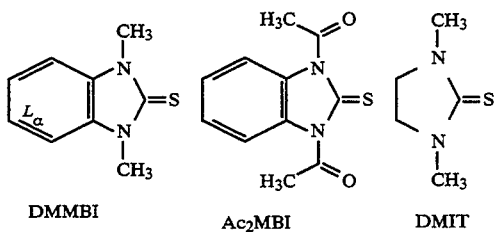

DMMBI   Ac₂MBI   DMIT

The examples show that DMMBI, DMIT and Ac₂-MBI, which are incapable of forming sulfenic acid metabolites, because of their N,N'-disubstitution, are not suicide inhibitors and block only reactions involving iodide ion oxidation via an alternate substrate mechanism. It is believed that the inability of N,N'-disubstituted thiocarbamides to form sulfenic acid metabolites allows therapies which are less toxic to non-target organs such as the liver and bone marrow. This is likely since the formation of reactive metabolites by oxidative enzymes in these organs and subsequent covalent binding to critical macromolecules are both causative factors in the liver and bone marrow toxicity. J. Utrecht, Chemical Research in Toxicology, Vol. 1, pp. 133–143 (1988). Such side effects limit the usefulness of currently used anti-hyperthyroid drugs, such as MMI and PTU.

This hypothesis is supported by the results discussed in Example 16 below. By employing $^{14}C$- and $^{35}S$-labelled compounds, the experimental results show that MBI and MMBI both become covalently bound to LPX under conditions where either suicide inactivation ($+H_2O_2$, $-KI$) or iodide ion oxidation are occurring ($+H_2O_2$, $+KI$). However, in the case of DMMBI, no binding over unstimulated controls occurs. This is consistent with metabolic conversion of MBI and MMBI, but not DMMBI, in the presence of iodide ion to reactive species which bind covalently to biological macromolecules.

The experimental protocols employed in the examples below provide methods for distinguishing between reversible and irreversible thiocarbamide inhibitors of LPX and TPX. On the basis of these experiments, N,N'-disubstituted thiocarbamide compounds such as DMMBI, DMIT and Ac₂MBI represent a novel class of new anti-hyperthyroid drugs that effectively block peroxidase-catalyzed iodination without causing enzyme inactivation.

The compounds employed in the present invention can be therapeutically administered to treat hyperthyroidism. Thus, the present invention provides compositions containing a therapeutically effective amount of at least one N,N'-disubstituted thiocarbamide compound, including the nontoxic addition salts thereof, which may, alone, serve to provide the desired anti-hyperthyroid therapeutic benefits. Such compositions can also be provided together with physiologically tolerable liquid, gel or solid carriers, diluents, adjuvants and excipients.

These compounds and compositions can be administered to mammals for veterinary use, such as for domestic animals, and clinical use in humans in a manner similar to other therapeutic agents. In general, the dosage required for therapeutic efficacy will vary according to the type of use and mode of administration, as well as the particularized requirements of individual hosts. In vitro experiments suggest that effective dosages and modes of administration for the compounds employed in the present invention are similar to currently used anti-hyperthyroid drugs such as MMI and PTU. MMI is typically administered orally in tablet form in an amount of 5 to 10 mg per dose, taken 3 times per day. PTU is similarly administered in a higher dose of 50 mg, taken 3 times per day. Determination of dose ranges in individual patients for the compounds of the present invention is more easily accomplished compared to previous drugs, since the problems associated with overdosing are less significant for the non-suicidal inhibitors.

The suitability of particular carriers for inclusion in a given therapeutic composition depends on the preferred mode of administration. For example, anti-hyperthyroid compositions are often formulated for oral administration. Such compositions are typically prepared either as liquid solution or suspensions, or in solid forms. Oral formulations usually include such normally employed additives such as binders, fillers, carriers, preservative, stabilizing agents, emulsifiers, buffers and excipients as, for example, pharmaceutical grades of mannitol, lactose, starch, magnesium stearate, sodium saccharin, cellulose, magnesium carbonate, and the like. These compositions; take the form of solutions, suspensions, tablets, pills, capsules, sustained release formulations, or powders, and typically contain 1%–95% of active ingredient, preferably 2%–70%.

Compositions of the present invention may also be prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

The following examples serve to illustrate certain preferred embodiments and aspects of the present invention and are not to be construed as limiting the scope thereof.

Experimental

In the experimental disclosure which follows, all weights are given in kilograms (Kg), grams (g), milligrams (mg), micrograms (μg) moles (mol) or millimoles (mmol). Concentrations are given as percent by volume (%), molar (M), millimolar (mM), micromolar (μM), or nanomolar (nM). Volumes are given in liters (L) or milliliters (mL), unless otherwise indicated. Temperatures are given in degrees Celsius (° C.). Molecular weight is abbreviated (MW). Lengths are given in meters (m), millimeters (mm), and microns (μm) and nanometers (nm).

The following abbreviations are used in the experimental examples below: 2,2'-azinobis[benzothiazoline-6-sulfonic acid] (ABTS); benzimidazole (BI); 1,3-dimethylbenzimidazolium (DMeBI+); 1,3-diacetylbenzimidazole-2-thione (Ac$_2$MBI); 1,3-dimethylimidazolidine-2-thione (DMIT); 1,3-dimethylbenzimidazole-2-thione (DMMBI); 2,2'dimethyl-2-silapentane-5-sulfonic acid (DSS); imidazolidine-2-thione (ETU); fast atom bombardment (FAB); liquid chromatography (LC); lactoperoxidase (LPX); benzimidazole-2-thione (MBI); 1-methylbenzimidazole (MeBI); 1-methylbenzimidazole-2-thione (MMBI); 1-methylimidazole-2-thione (MMI); mass spectrometry (MS); nuclear magnetic resonance (NMR); polyacrylamide gel electrophoresis (PAGE); 3-chloroperbenzoic acid (PBA); 5-phenylpentenyl alcohol (PPA); 5-phenylpentenyl hydroperoxide (PPHP); trifluoroacetic acid (TFA); thyroid peroxidase (TPX); thermospray (TSP).

Materials used in the examples below were obtained from the following sources. Bovine LPX, bovine liver catalase, glucose oxidase, 30% hydrogen peroxide, glucose, guaiacol, ABTS and deuterium oxide were purchased from Sigma Chemical Company. Selenium dioxide, MBI $^{13}CH_3I$ and PBA were purchased from Aldrich Chemical Company and PBA was purified as previously described by Fieset et al., Reagents for Organic Synthesis, Vol. I, pp.135–139, John Wiley and Sons, N.Y. (1967). LPX purity was checked by PAGE, as described by Doerge, D.R., et al. in, *Biochem. Pharmacol.*, Vol.36, pp.972–974 (1986). TPX was purified from hog thyroids obtained from a local slaughterhouse by published procedures. Doerge & Takazowa, *Chemical Research in Toxicology*, Vol. 3, pp. 98–101 (1990). TPX purity was determined by LC and its concentration determined spectophotometrically. Hydroperoxide concentrations were determined by iodometric titration, as described by Kolthoff, et al., in "Quantitative Chemical Analysis", Macmillan, London, pp.842–860 (1969). MMBI, and BI were synthesized by published procedures as described by Doerge, D.R., *Biochem*, Vol. 27, pp. 3697–3700 (1988) and were recrystallized from aqueous ethanol. MeBI was purified by distillation and DMeBI+was synthesized and purified by recrystallization from ethyl acetate/methanol. 1-$^{13}$C-MMBI was synthesized from $^{13}CH_3I$ according to the procedure disclosed by Doerge, D.R., in, *J. Lab. Comp. and Radiopharm.*, Vol.25, pp.985–990 (1988). PPHP and PPA were prepared, purified and analyzed as previously described by Doerge, *Biochem*, Vol.27, p.11 (1988). The methyl ester of 1-methyl-benzimidazole-2-sulfinic acid was prepared by addition of hydrogen peroxide (5 equivalents of a 10 M solution) to MMBI (0.1 M) in methanol. The products, MeBI and the ester, were obtained following preparative TLC on silica (Uniplate, Analtech Co., Newark, DL) using 5% methanol/-chloroform as eluant.

Products and starting materials were quantitated by LC using a Perkin Elmer 410 pump and LC95 UV detector by comparing peak heights with those generated by known amounts of standards. MBI was chromatographed on Novapak silica (4 micron, 8×100 mm cartridge, Waters Associates, Milford, MA) with 25% acetonitrile/water containing 0.1% tri-ethylamine, a flow rate of 1.5 ml/min and detection at 305 nm. MMBI and DMMBI were chromatographed on Novapak C18 (4 micron, 8×100 mm cartridge, Waters Associates) with 25 or 45% acetonitrile/water, respectively, 1.5 ml/min flow rate and detection at 305 nm. Structural characterization of all inhibitors and metabolites was made using particle beam or TSP/LC/MS.

Inhibition Studies

EXAMPLE 1

Figure 2:
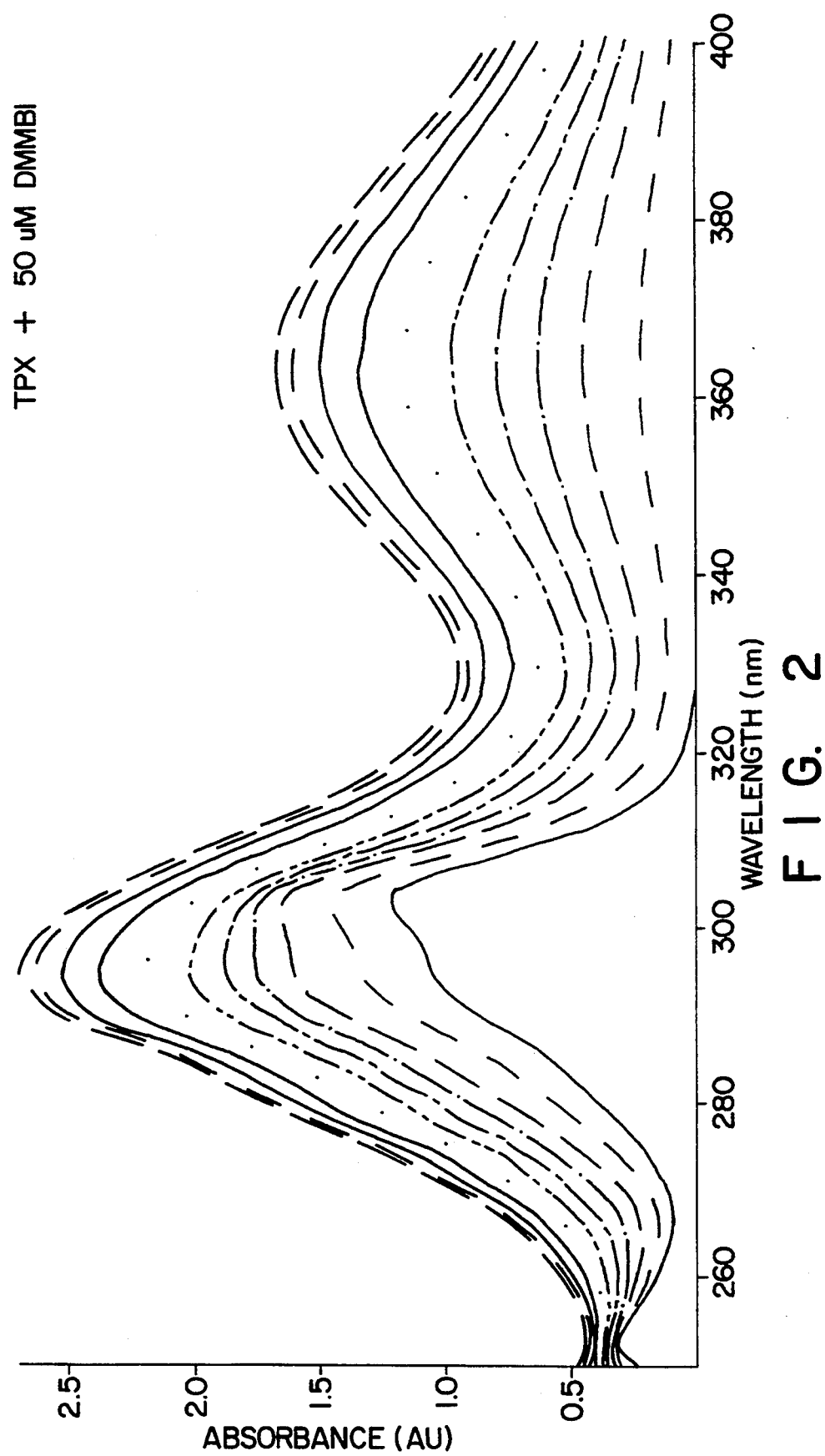
FIG. 2 is a spectrophotometric plot. Repeated scans show depletion of DMMBI by TPX in the presence of iodide ion and hydrogen peroxide.

DMMBI was synthesized according to a published method. Duffin et al., J. Chem. Soc., Part II, pp.364–365 (1956). Samples including TPX, $H_2O_2$, and I$^-$were incubated with and without DMMBI. Triiodide formation was observed spectrophotometrically with respect to time. The results, as shown in FIG. 1, indicate that the presence of DMMBI causes a lag in triiodide formation, followed by an increase in the rate of triiodide formation approximating the control rate. The data in the inset table in FIG. 1 shows that 100 μM DMMBI does not inactivate TPX in a 1 minute incubation period. DMMBI consumption was followed spectrophotometrically by repeated scanning as shown in FIG. 2.

EXAMPLE 2

Figure 3:
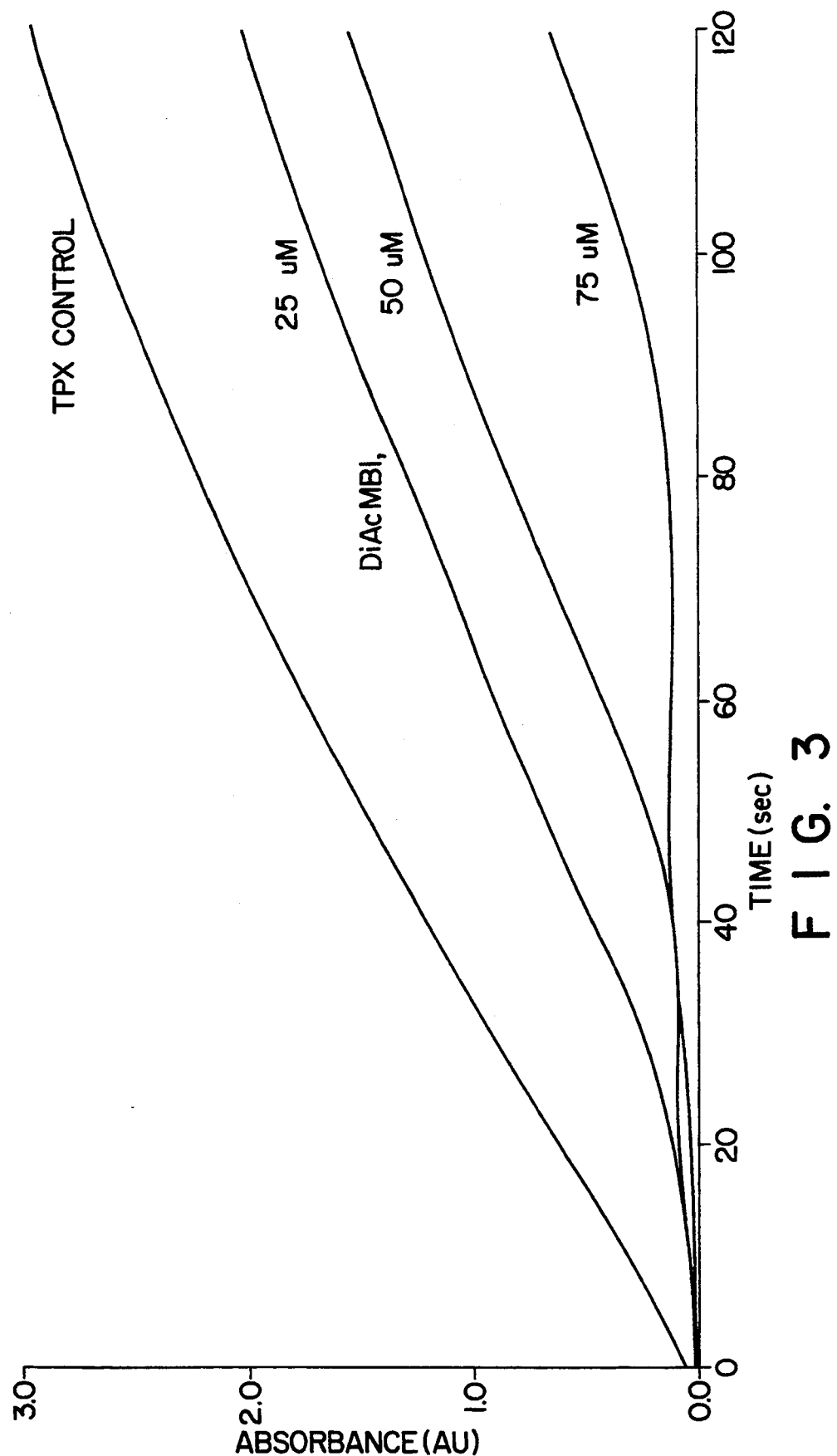
FIG. 3 is a graphic plot of spectrophotometric absorbance vs. time=showing TPX-catalyzed iodination inhibition by varying quantities of 1,3-diacetylbenzimidazoline-2-thione ($Ac_2MBI$).

1,3-diacetyl MBI (Ac$_2$MBI) was synthesized according to the method published by Doerge et al., Syn. Comm., Vol. 21, pp. 1789–1795 (1991). The identity of the synthesized product was verified by performing melting point, NMR and MS spectrometric analyses. Varying quantities of Ac$_2$MBI were incubated with TPX, $H_2O_2$, and I$^-$. Triiodide formation was observed spectrophotometrically as a function of time. The data, as shown in FIG. 3, indicates that Ac$_2$MBI exhibits similar inhibition of triiodide formation as was observed with DMMBI in example 1. Inhibition is characterized by an initial lag phase which is dependent on the amount of thione used. After the lag phase the triiodide formation rate increases to approximately the control rate.

EXAMPLE 3

DMIT was synthesized according to the published method by Maier, Helv. Chim. Acta, Vol. 53, p. 1417 (1970). Varying quantities of DMIT were incubated with peroxidase, $H_2O_2$ and I$^-$. Triiodide formation was observed spectrophotometrically as a function of time. The results obtained with DMIT were substantially the same as reported for DMMBI in Example 1 and Ac$_2$-MBI in Example 2. An initial lag phase was dependent on the amount of thione used, followed by a rate increase to approximately the control rate.

Chemical Oxygenation Studies

Oxidation Stoichiometry for MBI, MMBI and DMMBI

EXAMPLE 4

Oxidation stoichiometries were determined for the thione compounds MBI, MMBI and DMMBI by incubating the thiones with varying amounts of PBA (0–250μM). The rapid reaction (t$_½$<10 s at 25° C.) of benzimidazole-2-thiones with PBA in methanol provided a convenient method for determining oxidation stoichiometry.

Oxidation stoichiometries were determined spectrophoto, metrically, using a Hewlett Packard 8452A diode array spectrophotometer, by measuring thione concentration at 305 nm as a function of PBA concentration. Hydroperoxide content was determined iodometrically. Stoichiometries of substrate consumption/product formation were also determined by addition of limiting amounts of PBA to 100 $\mu$M MBI or MMBI in 50% methanol/pH 7 phosphate. The disappearance of thione and the production of BI, MeBI and bisulfite ion was determined after one hour at 25° C. The production of bisulfite ion was measured calorimetrically. The production of sulfate ion was determined by ion chromatography using a AS4A column (Dionex Co., Sunnyvale, CA) with a Dionex Gradient Pump Module and a Dionex CDM II conductivity detector equipped with an AMMS suppressor using 3 mM carbonate/bicarbonate buffer pH 10 as eluant at 2.0 ml/min. Reaction products were also monitored by $^1$H NMR performed at 300 MHz using a Nicolet NT300 or General Electric QE300 spectrometer DSS as a reference.

Figure 4:
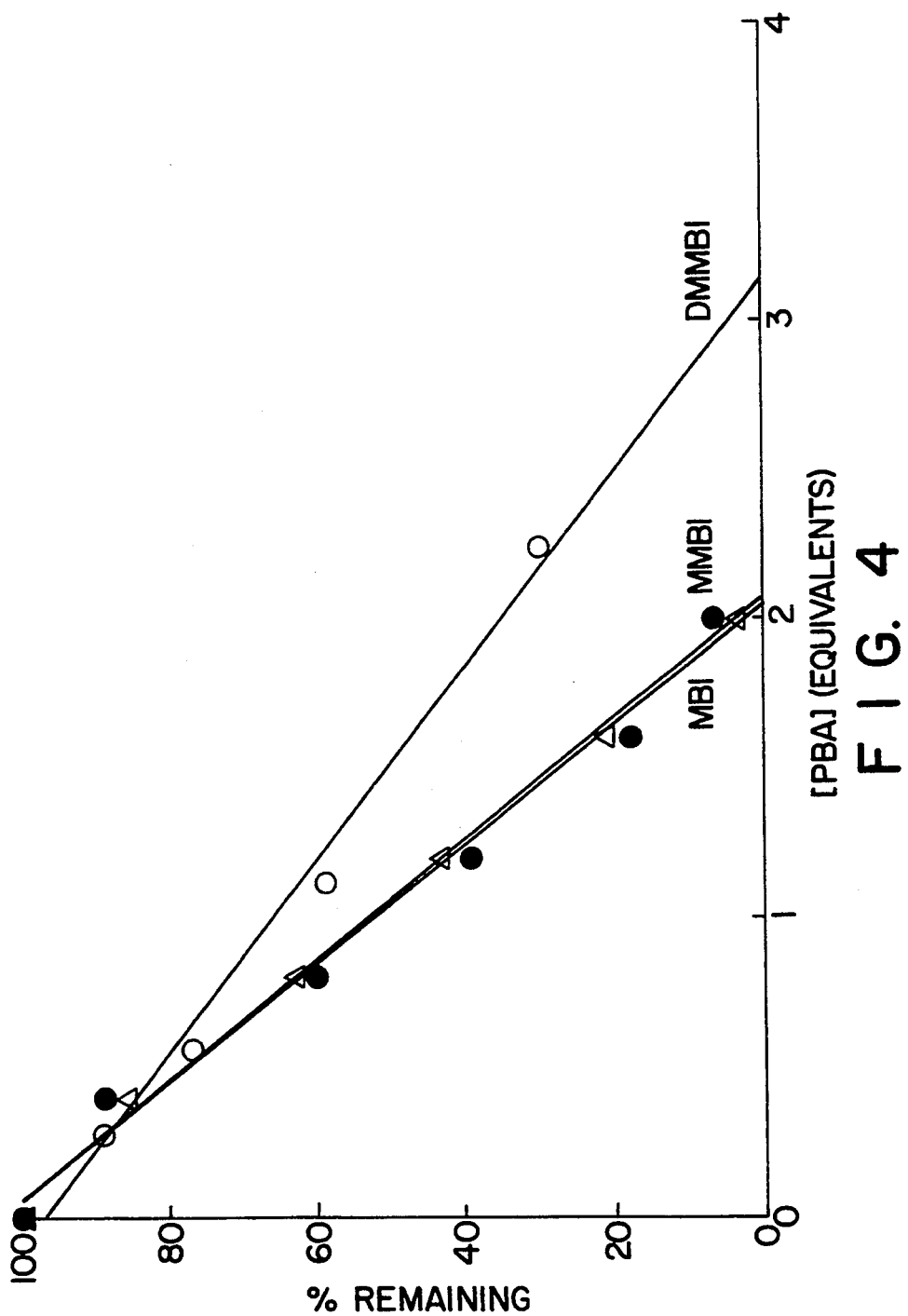
FIG. 4 is a graphic plot of percent thione oxidation vs. oxidant equivalents, comparing oxidation stoichiometry for benzimidazole-2-thione, (MBI), 1-methylbenzimidazole-2-thione (MMBI) and 1,3-dimethylbenzimidazole-2-thione (DMMBI).

The results of the experiment are shown in FIG. 4. MBI and MMBI required two moles of oxidant for total reaction in comparison to DMMBI which required three moles. In aqueous medium, 3 equivalents of PBA or hydrogen peroxide convert DMMBI to DMeBI- +and sulfate ions in essentially quantitative yield as determined by $^1$H-NMR and IC, respectively (data not shown). No bisulfite ion was detected from chemical oxidation of DMMBI.

EXAMPLE 5

The reaction of MBI and MMBI with PBA was also examined in aqueous buffered methanol. Thione (100 $\mu$M) was incubated with varying concentrations of PBA (0–200 $\mu$M). Reactant and product quantities were determined by LC as described in example 1. The ratios of product formation to thione consumption were calculated, and are reported below in Table 1. The values are averages of two slope determinations, i.e., moles of product formed or reactant consumed vs. moles of oxidant added, each determined from at least five data points.

TABLE 1

|  | MBI | MMBI |
|---|---|---|
| PBA/thione | 1.89 | 1.98 |
| benzimidazole/thione | 0.89 | 0.87 |
| bisulfite/thione | 0.72 | 0.72 |

The calculations shown in Table 1 indicate that the consumption of MBI and MMBI was accompanied by the nearly quantitative production of BI and MeBI, respectively, and bisulfite ion.

Characterizing MMBI Oxidation Products

EXAMPLE 6

The purpose of the following experiment was to further characterize the chemical structure(s) of MMBI oxidation products.

Figure 5:
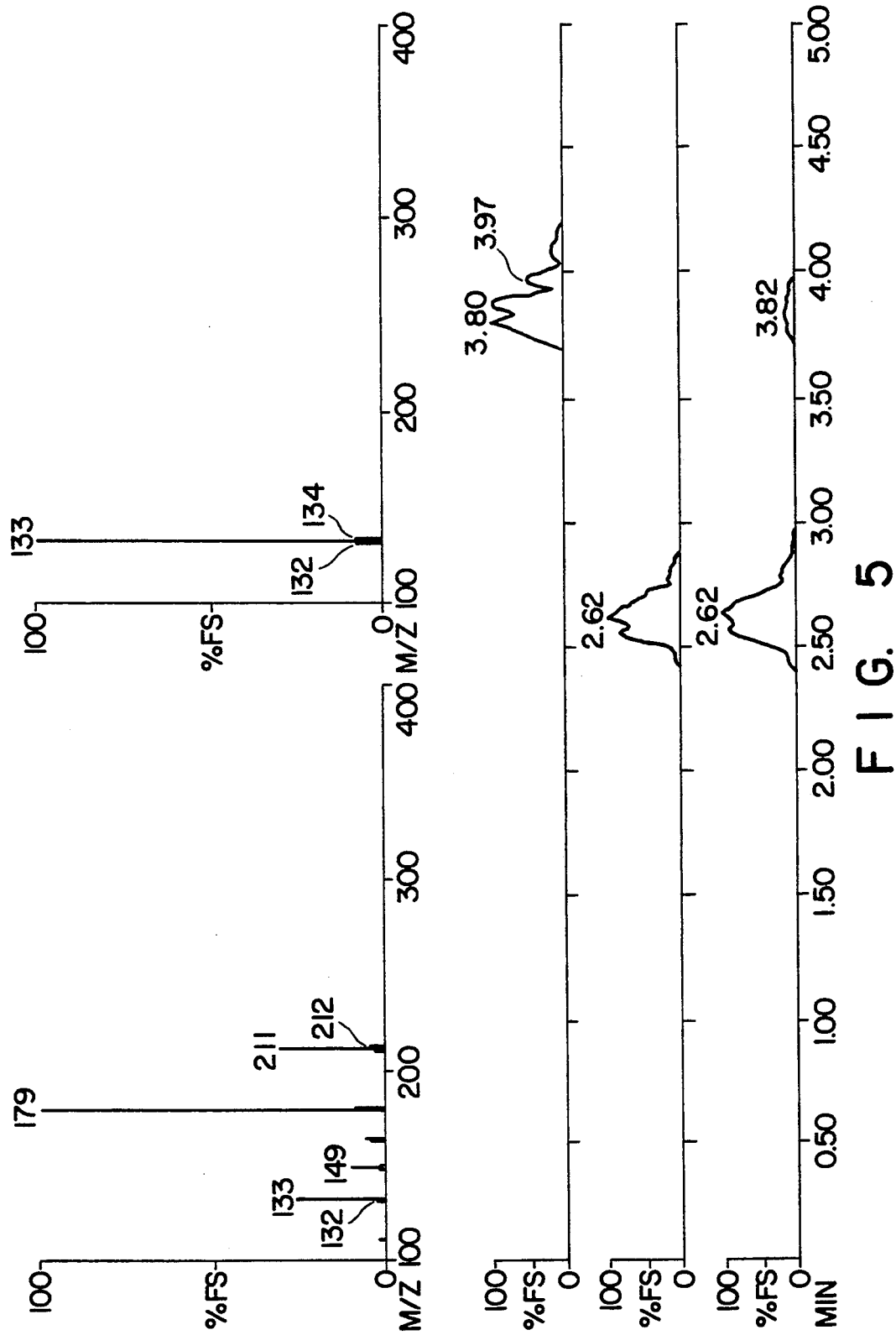
FIG. 5 is a graphic plot of a thermospray mass spectrometry analysis of the product of MMBI oxidation.

The products of MMBI oxidation were analyzed using GC-MS (data not shown) and TSP LC-MS, the results of which are shown in FIG. 5. MMBI was oxidized with excess hydrogen peroxide/SeO$_2$ in methanol at 0° C. and analyzed by TSP-MS. TSP LC-MS analysis was performed using a Hamilton PRP column with 50% acetonitrile/0.1 M ammonium acetate, pH 7.0 at a flow rate of 0.5 ml/min. The TSP capillary temperature was 190° C. and the source temperature was 250° C.

Mass chromatograms for the total ion current (TIC), MeBI (M+H+ =133) and the corresponding sulfinic acid methyl ester (M+H+ =211) are displayed along with the corresponding mass spectra in FIG. 5. In both cases, two distinct chromatographic peaks were observed with molecular ions corresponding to MeBI and benzimidazole-2-sulfinic acid methyl ester.

To further characterize the reaction, MMBI was synthesized with an NMR reporter group. NMR spectral data was generated at 76 MHz for $^{13}$C on either a Nicolet NT300 or General Electric QE300 spectrometer using DSS and dioxane as references. In contrast to the chromatographic results, $^{13}$C-NMR showed only one resonance (33.6 ppm) and it was different from those independently determined for the chromatographically observed products (MeBI, 31.2 and the sulfinic ester, 30.9 ppm). This product ($\delta^{13}$C=33.6 ppm) was stable indefinitely at 5° C. in methanol.

It is likely that the two observed chromatographic products from GC-MS and LC-MS result from pyrolysis at the elevated chromatographic temperatures although the same decomposition products are obtained upon exposure to silica at room temperatures. Addition of less than 2 equivalents of oxidant showed only the 33.6 ppm product and starting material with no intermediates observed.

EXAMPLE 7

The identity of the initial product from MMBI oxidation was investigated by MS using direct sample introduction and ionization by FAB. Analysis of the primary product using continuous-flow FAB-MS in positive and negative ion modes was useful because spectra are obtained after background subtraction of the intense matrix peaks. FAB-MS was performed using a continuous-flow (dynamic) probe with the mobile phase methanol/water/glycerol/TFA (45/45/10/0.1) in an 8kV Xe atom beam.

The reliability of mass assignments was further enhanced by using two isotopically substituted MMBI derivatives for the oxidation reaction (native, FIG. 6A, bottom panel and 1-CD$_3$-2-$^{13}$C- MBI, FIG. 6A, top panel). The isotopic shifts of 4 mass units for monomeric and 8 mass units for dimeric products aided in making assignments. Low intensity FAB+ions were observed at 405/413 m/z that correspond to the methanol adduct of the sulfinylsulfone. Ions at 327/335 m/z correspond to MMBI disulfide. It should be noted that all these ions are of low abundance as the FAB+base peak is 133 m/z (protonated MeBI). Analysis by dynamic FAB in the negative ion mode showed ions at 111 and 97 m/z with both isotopic variants of MMBI (see FIG. 6B, bottom panel). However, when the reaction was performed in CD$_3$OD instead of CH$_3$OH, the observed masses were 114 and 97 m/z (see FIG. 6B, top panel). These masses are consistent with $-$O$-$S$-$S$-$OCH$_3$ or $-$S$-$SO$-$OCH$_3$, methanolysis products that contain an oxidized disulfide linkage.

EXAMPLE 8

The kinetics of thione oxygenation were determined for MBI, MMBI and DMMBI. Oxygenation by hydrogen peroxide/TFA was measured spectrophotometrically (305 nm) at 25° C. by addition of thione (final concentration 25 μM) to hydrogen peroxide (34 mM) and TFA (163 mM) in methanol. MBI was observed to be the most reactive followed by MMBI and DMMBI, the relative rates being 2.3 to 1.3 to 1, respectively.

Enzymatic Oxygenation Studies
Effect of MBI, MMBI on Peroxidase Activity

EXAMPLE 9

Inhibition of LPX activity by thiones was determined from the kinetics of iodide ion, guaiacol or ABTS oxidation assays conducted at 25° C. Kinetic parameters of suicide inactivation were determined as previously described. Doerge, Biochem. Vol.27, pp.3697–3700 (1988).

The kinetics of LPX inactivation by MBI and MMBI were determined to be: $K_i=0.1$ and 274 nM and the partition ratios were approximately 3 and 35, respectively. Only MeBI and bisulfite ion have been identified as products which form concomitant to LPX inactivation by MMBI. The Kinetics for LPX inactivation by MBI and MMBI are respectively shown in FIGS. 7A and 7B.

Effect of DMMBI on Peroxidase Activity

EXAMPLE 10

Figure 8:
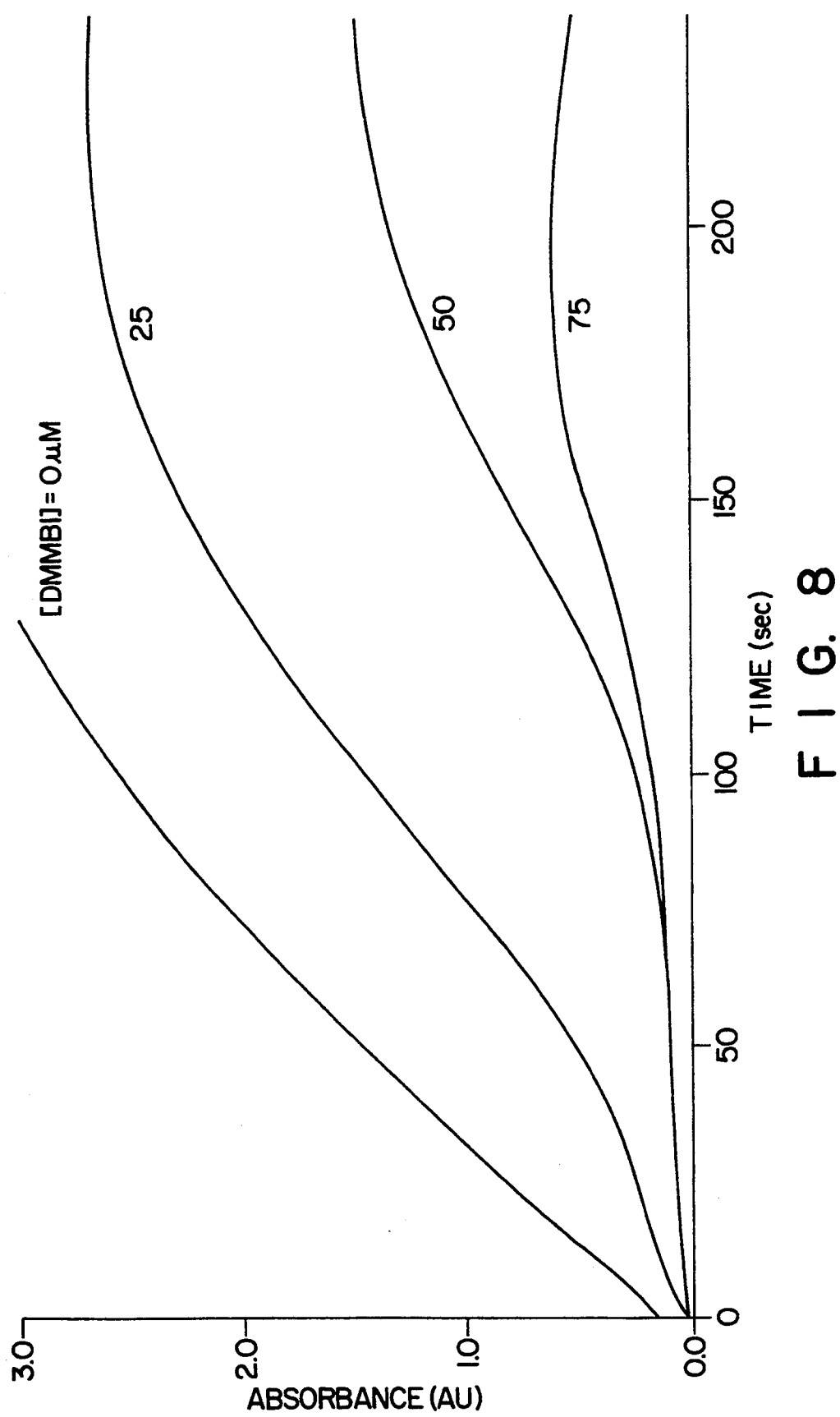
FIG. 8 is a graphic plot of spectrophotometric absorbance at 352 nm vs. time, showing the inhibitory effect of DMMBI on LPX catalyzed iodide oxidation.

The effect of DMMBI on LPX was tested. In contrast to MBI and MMBI, the presence of DMMBI in assay mixtures containing guaiacol or ABTS and LPX plus hydrogen peroxide did not reduce the rate of enzymatic oxidation of these two typical peroxidase substrates. However, the presence of DMMBI in assay media containing iodide ion caused marked inhibition of iodide ion oxidation (triiodide formation). As shown in FIG. 8, inhibition by DMMBI was characterized by a lag phase during which triiodide ion formation was retarded followed by an increased rate approaching the uninhibited oxidation rate. The decreases in rate and total $I_3^-$ formation are not the result of LPX inhibition, but instead relate to $H_2O_2$ depletion. Addition of an aliquot of $H_2O_2$ after maximal $I_3^-$ had occurred (in the plateau region of the curves) produced an additional burst of $I_3^-$ formation. The rate and magnitude of this response were equivalent for control (no DMMBI) and DMMBI incubations. Identical results were observed when the same experiment was performed with DMIT instead of DMMBI. The lag period was proportional to the concentration of DMMBI, but inversely related to the concentration of iodide ion or hydrogen peroxide in the assay mixture (data not shown). The results in this experiment were similar to the data shown in FIGS. 1 and 3 for TPX, confirming that LPX is a valid model for TPX inhibition by N,N'-disubstituted thiocarbamides.

EXAMPLE 11

Repetitive spectrophotometric scans were performed during the lag phase of DMMBI-inhibited triiodide formation. DMMBI (100 μM) was incubated with LPX and a hydrogen peroxide generating system. Spectrophotometric scans were taken at 20 second intervals over the wavelength range 250–400nm. The absorption maxima are: DMMBI, 305nm; triiodide ion, 290 and 352 nm; DMeBI+, 270 and 278nm.

Figure 9:
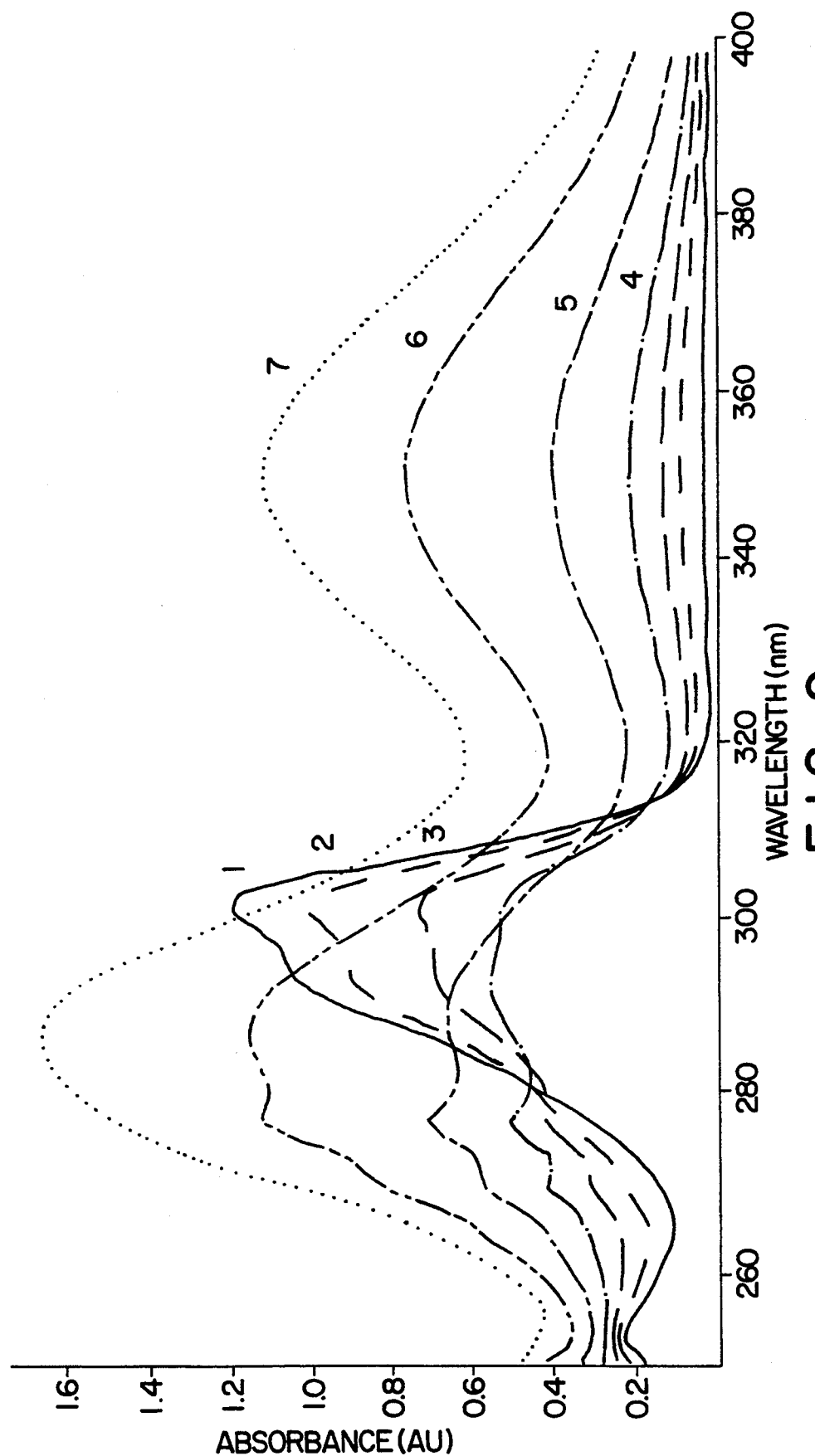
FIG. 9 is a graphic plot of spectrophotometric absorbance vs. wavelength at various times during the lag phase of iodide ion oxidation caused by DMMBI inhibition.

The results, as shown in FIG. 9, indicate that the lag in triiodide formation (290, 352 nm) is accompanied by disappearance of DMMBI (305 nm). Production of triiodide begins only after DMMBI has been consumed and the absorption bands at 270 and 278 nm indicate the presence of DMeBI+ as an oxidation product. The results in this experiment were similar to the data shown in FIG. 2 for TPX. However, this data is more definitive since detergents present in the TPX incubations interfere in the spectral region of interest.

EXAMPLE 12

The following experiment was performed to determine the effect of DMMBI oxidation on LPX activity. LPX (0.1 μM, final concentration) was incubated with hydrogen peroxide (100 μM), iodide ion (5 mM) and DMMBI (100 μM), as indicated in Table 2. After a 100 second incubation at 25° C., an aliquot was diluted 200-fold and the iodide ion oxidation activity determined. Values shown in Table 2, are averages +/− standard deviations (n=4) of the percentage relative to untreated LPX. Similar results were obtained for DMIT under the same conditions (data not shown).

TABLE 2

| | Rate (% of control) |
|---|---|
| LPX + DMMBI | 100 ± 4% |
| LPX + H$_2$O$_2$ | 99 ± 4% |
| LPX + H$_2$O$_2$ + DMMBI | 104 ± 6% |
| LPX + H$_2$O$_2$ + DMMBI + I$^-$ | 107 ± 6% |
| LPX + H$_2$O$_2$ + I$^-$ | 104 ± 6% |

Enzymatic oxidation of DMMBI by LPX/hydrogen peroxide has been shown to occur only in the presence of iodide ion (data not shown). Under conditions where DMMBI is converted to DMeBI+ and iodide ion oxidation is completely blocked, as in experimental Example 9, no loss of enzymatic activity was detected following 1/200 dilution. In the absence of iodide ion, incubation of LPX/hydrogen peroxide with DMMBI or DMIT did not cause any loss of enzymatic activity. See FIG. 1 for similar results with TPX. These results are in contrast to the actions of MBI and MMBI which produce rapid, irreversible loss of LPX and TPX activity under similar conditions.

EXAMPLE 13

The distinct methyl and aromatic proton resonances of DMMBI and DMeBI+ in the $^1$H-NMR spectrum provide a sensitive method to detect enzymatic transformation of DMMBI. DMMBI (100 μM) was incubated with LPX (50 μM), iodide ion (5 mM) and hydrogen peroxide (300 μM) in 10 mls of 0.01 M phosphate buffer solution, pH 7.0. The solution was incubated at 25° C. for 1 min followed by addition of catalase. The sample was then lyophilized and analyzed by $^1$H-NMR. The solids were dissolved in 1 ml D$_2$O and lyophilized again. Proton-deuterium exchange was repeated twice more and the solids were dissolved in 0.5 ml D$_2$O containing DSS. The HOD peak was suppressed in a one pulse presaturation experiment where the HOD peak was irradiated for 2 sec prior to acquisition of sample resonances. The $^1$H-NMR spectra of DMeBI+ and DMMBI were similarly recorded in D$_2$O.

Figures 10A, 10B, 10C:
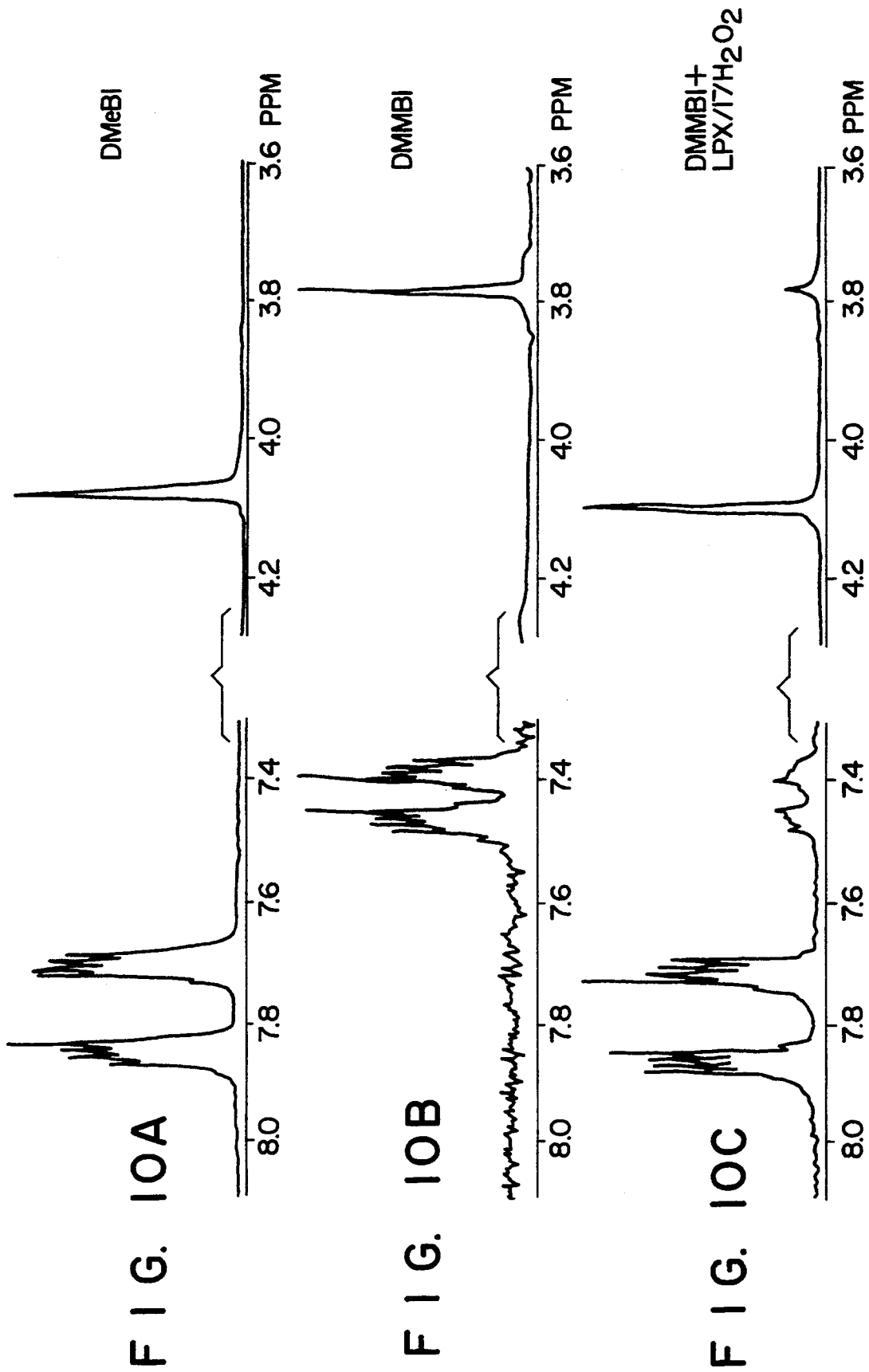
FIGS. 10A, 10B and 10C show graphic plots of $^1$H-NMR spectra for DMeBI, DMMBI and DMMBI+LPX/I$^-$/H$_2$O$_2$, illustrating enzymatic transformation of DMMBI.

FIG. 10 shows the $^1$H-NMR spectra of DMMBI, DMeBI+ and a reaction mixture containing LPX, DMMBI and iodide ion initiated by addition of 3 equivalents of hydrogen peroxide. DMeBI+ was the only product observed. Control experiments were conducted under the same conditions except that: a) no iodide ion was present b) no LPX was present c) no hydrogen peroxide was present. In all cases, no conversion of DMMBI to DMeBI+ was observed. Formation of DMeBI was confirmed spectrophotometrically in accordance with the procedure discussed in Example 9.

When triiodide ion was formed by addition of hydrogen peroxide to LPX and iodide ion, addition of DMMBI caused rapid quenching of triiodide (ca. 1 sec) and DMeBI+ was the sole product. Triiodide produced by addition of $I_2$ to aqueous iodide ion reacted identically with DMMBI.

EXAMPLE 14

PPHP is a chromophoric hydroperoxide interchangeable with hydrogen peroxide in many peroxidase-catalyzed reactions. LPX-catalyzed turnover of PPHP gives PPA, the corresponding alcohol, which can be quantitated by HPLC. The use of PPHP permits a direct correlation of LPX-catalyzed substrate consumption and product formation with actual hydroperoxide turnover.

It was determined that, under conditions where PPHP-supported LPX-catalyzed iodination was inhibited by DMMBI, 3.2±0.2 moles of PPA were formed and 3.2 moles of PPHP consumed per mole of DMMBI consumed. It was also determined that 3.2 moles of sulfate ion were formed per mole of hydrogen peroxide added to a mixture of LPX, iodide ion and DMMBI.

EXAMPLE 15

In this experiment the effect of DMMBI on tyrosine iodination catalyzed by LPX was determined. Tyrosine was incubated with LPX, $I^-$, $H_{O2}$ and DMMBI (FIG. 11, panel A). A control was run without DMMBI (FIG. 11, panel B). The chromatogram from standards monoiodotyrosine (MIT) diiodotyrosine (DIT) and tyrosine (Tyr) are shown in FIG. 11, panel C. The chromatographic results shown in FIG. 11 indicate that DMMBI inhibits tyrosine iodination catalyzed by LPX. Similar results were observed with TPX (data not shown).

EXAMPLE 16

LPX-mediated covalent binding of $^{14}C$- and $^{35}S$-labelled thiocarbamides to LPX under iodide-dependent and -independent conditions was measured. The results are shown in FIG. 12. These results show that MBI and MMBI become covalently bound to LPX under conditions where either suicide inactivation or iodide ion oxidation are occurring ($+H_2O_2$ vs. $+H_2O_2 +KI$). However, in the case of DMMBI, no binding over unstimulated controls occurs. This result supports the conclusion that DMMBI is not a suicide inhibitor and does not bind covalently to peroxidases during iodide ion oxidation.

To summarize, MBI and MMBI bind covalently to LPX and TPX in the presence of $H_2O_2$ and cause irreversible inactivation. DMMBI does not bind covalently to LPX in the presence of $H_2O_2$ and does not cause inactivation of LPX or TPX. The binding observed in the presence of iodide ion is consistent with peroxidase-mediated metabolism of MBI and MMBI, but not DMMBI, to reactive species which bind covalently to biological macromolecules.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the claims.

What is claimed is:

1. A method for treating hyperthyroidism in a patient by reversibly inhibiting thyroid peroxidase activity without causing adverse side effects comprising the steps of:

providing a compound in accordance with the following formula:

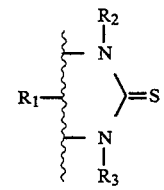

wherein $R_1$ is selected from the group consisting of:

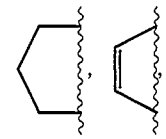

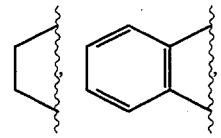

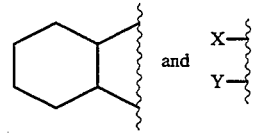

wherein $R_2$ and $R_3$ are independently selected from the group consisting of $C_1-C_6$ alkyl moieties and X and Y are independently selected from the group consisting of $C_1-C_6$ alkyl and acyl moieties; and administering a therapeutically effective dose of said compound to the patient.

2. The method of claim 1 further comprising the step of producing a therapeutic composition by combining said compound with a suitable carrier prior to said administering step.

3. The method of claim 1 wherein $R_2$ and $R_3$ of said compound are each methyl.

4. The method of claim 3 wherein $R_1$ is

5. The method of claim 3 wherein $R_1$ is

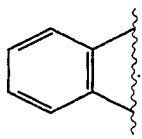

6. The method of claim 1 wherein $R_1$ is

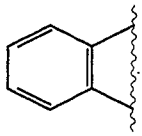

7. A method for treating hyperthyroidism in a patient without causing adverse side effects comprising the steps of:
provef providing a compound in accordance with the following formula:

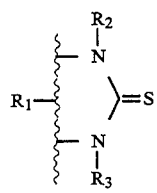

wherein $R_1$ is selected from the consisting of:

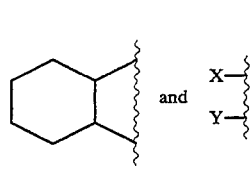

wherein $R_2$ and $R_3$ are independently selected from the group consisting of $C_1$–$C_6$ alkyl moieties and X and Y are independently selected from the group consisting of $C_1$–$C_6$ alkyl and acyl moieties; and
reversibly inhibiting the patient's thyroid hormone synthesizing activity by administering a therapeutically effective dose of said compound.

8. The method of claim 7 further comprising the step of producing a therapeutic composition by combining said compound with a suitable carrier prior to said administering step.

9. The method of claim 7 wherein $R_2$ and $R_3$ of said compound are each methyl.

10. The method of claim 9 wherein $R_1$ is

11. The method of claim 9 wherein $R_1$ is

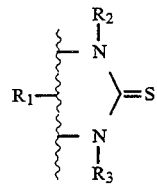

12. The method of claim 7 wherein $R_1$ is

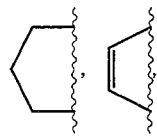

13. A composition for treating hyperthyroidism by reversibly inhibiting thyroid peroxidase activity without causing adverse side effects comprising:
a therapeutically effective dose of a compound which cannot form a sulfenic acid or methimazole in accordance with the following formula:

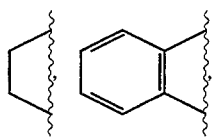

wherein $R_1$ is selected from the group consisting of:

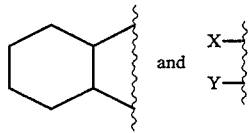

wherein $R_2$ and $R_3$ are independently selected from the group consisting of $C_1$–$C_6$ alkyl moieties and X and Y are independently selected from the group and consisting of $C_1$–$C_6$ alkyl and acyl moieties; and
a suitable carrier combined with said therapeutically effective dose of said compound.
14. The composition of claim 13 wherein $R_2$ is methyl and $R_3$ is methyl.
15. The composition of claim 14 wherein $R_1$ is
16. The composition of claim 14 wherein $R_1$ is
17. The composition of claim 13 wherein $R_1$ is
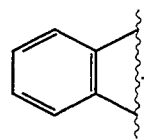
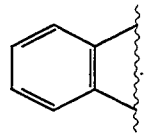
* * * * *